United States Patent [19]

Florvall et al.

[11] 4,232,037
[45] Nov. 4, 1980

[54] 2,6-DIALKOXYBENZAMIDES, INTERMEDIATES, PHARAMACEUTICAL COMPOSITIONS AND METHODS FOR TREATMENT OF PSYCHOTIC DISORDERS

[75] Inventors: Gosta L. Florvall; Sven O. Ogren, both of Södertalje, Sweden

[73] Assignee: Astra Läkemedel Aktiebolag, Södertälje, Sweden

[21] Appl. No.: 18,784

[22] Filed: Mar. 8, 1979

[30] Foreign Application Priority Data

Mar. 23, 1978 [SE] Sweden .......................... 7803411

[51] Int. Cl.³ .................... A61K 31/40; C07D 207/08
[52] U.S. Cl. ............................ 424/274; 260/326.47; 562/474
[58] Field of Search ................ 260/326.47; 424/274

[56] References Cited

U.S. PATENT DOCUMENTS

| | | | |
|---|---|---|---|
| 3,342,826 | 9/1967 | Miller et al. | 260/326.47 |
| 3,862,139 | 1/1975 | Podesva et al. | 424/274 |
| 4,021,567 | 5/1977 | Kaplan et al. | 424/274 |
| 4,029,673 | 6/1977 | Bulteau et al. | 260/326.47 |

FOREIGN PATENT DOCUMENTS

| | | | |
|---|---|---|---|
| 695272 | 3/1967 | Belgium | 260/326.47 |
| 60756 | 11/1965 | German Democratic Rep. | 260/326.47 |
| 67123 | 6/1969 | German Democratic Rep. | 260/326.47 |
| 2459221 | 6/1975 | Fed. Rep. of Germany | 260/326.47 |
| 2556457 | 6/1976 | Fed. Rep. of Germany | 260/326.47 |

OTHER PUBLICATIONS

Derwent Spec. No. 1588z; Werck & Co. (1/14/65).
Derwent Spec. No. 8188r (8/1/68).

*Primary Examiner*—Mary C. Lee
*Attorney, Agent, or Firm*—Brumbaugh, Graves, Donohue & Raymond

[57] ABSTRACT

A compound of the formula

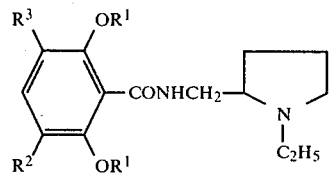

wherein $R^1$ is an alkyl group with 1-3 carbon atoms, $R^2$ and $R^3$ are the same or different and each is hydrogen, chlorine or bromine; and pharmaceutically acceptable salts and optical isomers thereof; methods and intermediates for the preparation of the compounds; pharmaceutical preparations containing them and their medical use for the treatment of psychoses.

13 Claims, No Drawings

2,6-DIALKOXYBENZAMIDES, INTERMEDIATES, PHARAMACEUTICAL COMPOSITIONS AND METHODS FOR TREATMENT OF PSYCHOTIC DISORDERS

FIELD OF THE INVENTION

This invention relates to new 2,6-dialkoxybenzamides and to a method for their preparation. The invention also relates to pharmaceutical compositions containing the 2,6-dialkoxybenzamides and to methods for their therapeutic use.

PRIOR ART

Sulpiride, (U.S. Pat. No. 3,342,826) with the formula

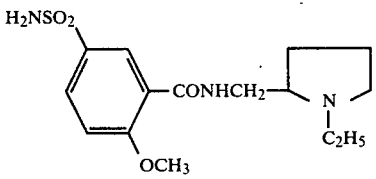

is a recently marketed antipsychotic agent. Sulpiride produces weak extrapyramidal side effects in humans and weak catalepsy in experimental animals.

DESCRIPTION OF THE INVENTION

Although sulpiride has valuable properties we have found compounds which are still better. Remarkable is the superiority of the compounds of this invention over sulpiride after oral administration.

These new antipsycotic compounds are characterized by the general formula

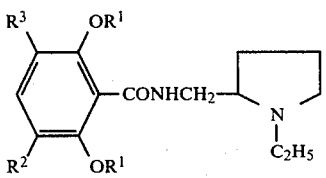

wherein $R^1$ represents an alkyl group with 1-3 carbon atoms, $R^2$ and $R^3$ are the same or different and each represents a hydrogen, chlorine or bromine atom.

Pharmaceutically acceptable salts of the compounds of the formula I are also comprised by this invention.

Alkyl groups with 1-3 carbon atoms are methyl, ethyl, n-propyl and isopropyl.

The new compounds of this invention may be used therapeutically as the racemic mixtures of (+)- and (−)-forms, which are obtained by synthesis. They may also be resolved into the corresponding enantiomers which, likewise, may be used in therapy. The (+)-and (−)-forms may also be obtained by reaction of an optically active salt of 2-(aminomethyl)-1-ethylpyrrolidine with the dialkoxybenzamide moiety.

This invention also takes into consideration that compounds which structurally deviate from the formula I after administration to a living organism may be transformed therein to a compound of the formula I and in this structural form exerting their effects. This consideration is a further aspect of this invention.

The compounds of this invention may be administered in the form of free bases or their salts with non-toxic acids. Some typical examples of these salts are the hydrobromide, hydrochloride, phosphate, sulphate, citrate, and tartrate.

PHARMACEUTICAL PREPARATIONS

In clinical practice the compounds of the present invention will normally be administered orally, rectally or by injection in the form of pharmaceutical preparations comprising the active ingredient either as a free base or as a pharmaceutically acceptable non-toxic, acid addition salt, e.g. the hydrochloride, hydrobromide, lactate, acetate, sulphate, sulphamate and the like in association with a pharmaceutically acceptable carrier. Accordingly, terms relating to the novel compounds of this invention whether generically or specifically are intended to include both the free amine base and the acid addition salts of the free base, unless the context in which such terms are used, e.g. in the specific examples would be inconsistent with the broad concept.

The carrier may be a solid, semisolid or liquid diluent or capsule. These pharmaceutical preparations constitute a further aspect of this invention. Usually the active substance will constitute between 0.1 and 99% by weight of the preparation, more specifically between 0.5 and 20% by weight for preparation intended for injection and between 2 and 50% by weight for preparations suitable for oral administration.

To produce pharmaceutical preparations containing a compound of the invention in the form of dosage units for oral application, the selected compound may be mixed with a solid pulverulent carrier, e.g. lactose, saccharose, sorbitol, mannitol, starches such as potatoe starch, corn starch or amylopectin, cellulose derivatives, or gelatine, and a lubricant such as magnesium stearate, calcium stearate, polyethylene glycol waxes, and the like, and then compressed to form tablets. If coated tablets are required, the cores, prepared as described above, may be coated with a concentrated sugar solution which may contain, e.g. gum arabic, gelatine, talcum, titanium dioxide, and the like. Alternatively, the tablet can be coated with a lacquer dissolved in a readily volatile organic solvent or mixture of organic solvents. Dyestuffs may be added to these coatings in order to readily distinguish between tablets containing different active substances or different amounts of the active compound.

For the preparation of soft gelatine capsules (pearl-shaped closed capsules) consisting of gelatine and for example, glycerol or similar closed capsules, the active substance may be admixed with a vegetable oil. Hard gelatine capsules may contain granulates of the active substance in combination with solid, pulverulent carriers such as lactose, saccharose, sorbitol, mannitol, starches (e.g. potatoe starch, corn starch or amylopectin), cellulose derivatives or gelatine.

Dosage units for rectal application can be prepared in the form of suppositories comprising the active substance in admixture with a neutral fatty base, or gelatine rectal capsules comprising the active substance in admixture with vegetable oil or paraffin oil.

Liquid preparations for oral application may be in the form of syrups or suspensions for example, solutions containing from about 0.2% to about 20% by weight of the active substance herein described, the balance being sugar and a mixture of ethanol, water, glycerol, and propyleneglycol. Optionally such liquid preparations may contain colouring agents, flavouring agents, saccharine and carboxymethyl-cellulose as a thickening agent.

Solutions for parenteral applications by injection can be prepared in an aqueous solution of a water-soluble pharmaceutically acceptable salt of the active substance preferably in a concentration of from about 0.5% to about 10% by weight. These solutions may also contain stabilizing agents and/or buffering agents and may conveniently be provided in various dosage unit ampoules. Suitable peroral daily doses of the compounds of the invention are 100–500 mg, preferably 200–300 mg.

PREFERRED EMBODIMENT

The preferred compounds of the invention have the formulas

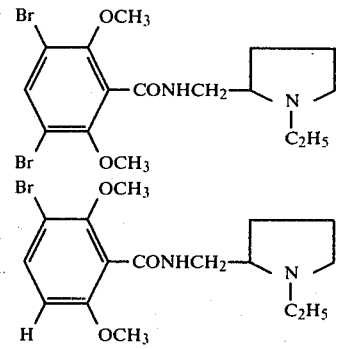

Particularly the (−)-forms of the above compounds are preferred.

METHOD OF PREPARATION

The compounds of the formula I of this invention can be prepared by reaction of a derivative of 2,6-dialkoxybenzoic acid of the formula

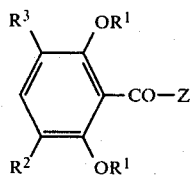

II wherein $R^1$ represents an alkyl group with 1–3 carbon atoms, $R^2$ and $R^3$ are the same or different and each represents a hydrogen, chlorine or bromine atom and —CO—Z represents a reactive group capable of reacting with an amino group under formation of an amide moiety, with 2-(aminomethyl)-1-ethylpyrrolidine of the formula

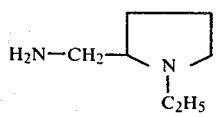

The reaction is carried out in a suitable solvent, such as diethyl ether, acetone or methyl ethyl ketone. The resulting amine hydrochloride salt is readily recovered e.g. by filtration. Alternatively the obtained salt is dissolved in water and converted to the free base using conventional techniques, such as the addition of sodium hydroxide solution.

The acylating group —CO—Z in formula II may be an acid chloride group, or a group functioning in the same way, e.g. an acid bromide, an acid azid, an anhydride, a mixed anhydride formed with an inorganic acid or an organic acid such as an alkyl carbonic acid, a carbonic acid. Alternatively, the acid derivate (pref. an acid chloride) is reacted with the amine in the presence of a base e.g. triethylamine. The group —CO—Z may also be an ester group, e.g. alkyl ester such as methyl ester.

INTERMEDIATES

The free carboxylic acid corresponding to the derivative of formula II is prepared by the halogenation of a 2,6-dialkoxybenzoic acid with an appropriate halogenating agent, e.g. free halogen or sulphuryl chloride. The preparation routes are illustrated below.

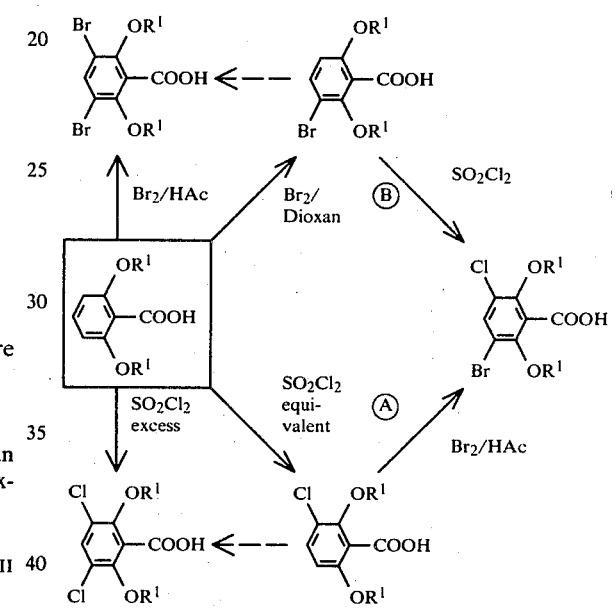

The free carboxylic acid is then converted by conventional means to the corresponding derivative of the formula II.

The compound of the formula

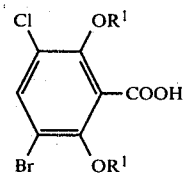

has not previously been described in the literature.

WORKING EXAMPLES

Preparation of starting materials

Example 1. 3-Bromo-2,6-dimethoxybenzoic acid

A solution of 15 ml of bromine (0.3 mol) in 50 ml of chloroform is added dropwise while stirring and cooling in ice to 54.9 g (0.3 mol) of 2,6-dimethoxybenzoic acid in 150 ml of dioxan. The solution is left at room temperature overnight. The solvent is evaporated and the residue recrystallized from aqueous ethanol. Yield: 59.3 g, m.p. 144°–45° C.

Example 2. 3-Chloro-2,6-dimethoxybenzoic acid

A solution of 16.2 ml (0.2 mol) of sulphuryl chloride in 100 ml of chloroform is added dropwise while stirring to a solution of 36.4 g (0.2 mol) of 2,6-dimethoxybenzoic acid in 300 ml of chloroform. The mixture is heated for 0.5 h at 50° C. and left overnight at room temperature. The solvent is evaporated and the residue recrystallized from isopropyl ether—light petroleum. Yield: 35.4 g, m.p. 132°–33° C.

Example 3. 3,5-Dibromo-2,6-dimethoxybenzoic acid

A solution of 12 ml (0.23 mol) of bromine in 50 ml of acetic acid is added dropwise while stirring to a mixture of 18.2 g (0.1 mol) of 2,6-dimethoxybenzoic acid and 21 g (0.25 mol) of dry sodium acetate in 150 ml of acetic acid. The mixture is stirred over night at room temperature and is then poured into 1 liter of ice water. The precipitate is filtered off, washed with water and dried. The crude compound is purified by recrystallization from light petroleum. Yield: 14.1 g, m.p. 108°–10° C.

Example 4. 3,5-Dichloro-2,6-dimethoxybenzoic acid

A solution of 20 ml (0.25 mol) of sulphuryl chloride in 50 ml of chloroform is added dropwise to a solution of 15.0 g (0.08 mol) 2,6-dimethoxybenzoic acid in 100 ml of chloroform. The solution is left over night at room temperature and is then refluxed for 0.5 h. The solvent is evaporated and the residue recrystallized twice from light petroleum. Yield: 17.0 g, m.p. 98°–100° C. (first recrystallization). Yield: 12.0 g, m.p. 102°–103° C. (second recrystallization).

Example 5. 3-Bromo-5-chloro-2,6-dimethoxybenzoic acid

A. From 3-chloro-2,6-dimethoxybenzoic acid

A solution of 1.5 ml (0.03 mol) of bromine in acetic acid is added to a mixture of 2.7 g (0.01 mol) of 3-chloro-2,6-dimethoxybenzoic acid and 3.0 g of anhydrous sodium acetate in 50 ml of acetic acid. The mixture is left at room temperature over night and is then poured into 300 ml of ice water. The precipitate is filtered off, washed with water, dried and recrystallized from isopropyl ether—light petroleum. Yield: 0.5 g, m.p. 99°–100° C.

Analysis, calculated for $C_9H_8BrClO_4$: C 36.58, H 2.73, Br 27.04, Cl 12.00, O 21.65. Found: C 36.6, H 2.51, Cl 11.8.

B. From 3-bromo-2,6-dimethoxybenzoic acid

A solution of 40 ml (0.5 mol) of sulphuryl chloride in 100 ml of chloroform is added dropwise to a solution of 26.1 g (0.1 mol) of 3-bromo-2,6-dimethoxybenzoic acid in 150 ml of chloroform. After a night at room temperature the solution is refluxed for 45 minutes. The solvent is evaporated and the residue recrystallized from isopropyl ether - light petroleum. Yield: 23.5 g, m.p. 98.5°–100° C.

PREPARATION OF END COMPOUNDS

Example 6. N-Ethyl-2-(2,6-dimethoxybenzamidomethyl) pyrrolidine hydrochloride 30 ml of thionyl chloride is added to 18.2 g (0.1 mol) of 2,6-dimethoxybenzoic acid. The mixture is heated on a steam bath for 30 minutes. To the solution is added 50 ml of toluene. The solvent and excess thionyl chloride is evaporated at reduced pressure. The residue is dissolved in 50 ml of dry methyl ethyl ketone. The solution is added dropwise while stirring to 12.8 g (0.1 mol) of 2-(aminomethyl)-1-ethyl-pyrrolidine in 50 ml methylethyl ketone. After the addition the mixture is stirred for 30 minutes at room temperature. The obtained precipitate is filtered off, washed with ether and recrystallized from ethanol - isopropyl ether. Yield: 26.7 g, m.p. 182°–84° C.

Example 7. N-Ethyl-2-(3-bromo-2,6-dimethoxybenzamidomethyl)-pyrrolidine hydrochloride 30 ml of thionyl chloride is added to 17.6 g (0.067 mol) of 3-bromo-2,6-dimethoxybenzoic acid. The mixture is heated on a steam bath for 30 minutes. To the solution is added 50 ml of toluene. The solvent and excess thionyl chloride is evaporated at reduced pressure. The residue is dissolved in 50 ml of dry methyl ethyl ketone. The solution is added dropwise while stirring to 9.23 g (0.072 mol) of 2-(aminomethyl)-1-ethylpyrrolidine in 50 ml of methyl ethyl ketone. After stirring for 30 minutes at room temperature 150 ml of ethyl ether is added. The obtained precipitate is filtered off, washed with ether and recrystallized twice from ethanol-isopropyl ether. Yield: 21.0 g, m.p. 182°–84° C. (first recrystallization). m.p. 184°–85° C. (second recrystallization).

Example 8. N-Ethyl-2-(3-chloro-2,6-dimethoxybenzamidomethyl)-pyrrolidine hydrochloride 30 ml of thionyl chloride is added to 17.0 g (0.078 mol) of 3-chloro-2,6-dimethoxybenzoic acid. The mixture is heated on a steam bath for 30 minutes. To the solution is added 50 ml of toluene. The solvent and excess thionyl chloride is evaporated at reduced pressure. The residue is dissolved in 50 ml of dry methyl ethyl ketone. The solution is added dropwise while stirring to 10.0 g (0.078 mol) of 2-(aminomethyl)-1-ethylpyrrolidine in 50 ml of methyl ethyl ketone. After stirring for 30 minutes at room temperature 150 ml of ether is added. The obtained precipitate is filtered off, washed with ether and recrystallized twice from ethanol - isopropyl ether. Yield: 21.3 g, m.p. 175°–77° C. (first recrystallization). m.p. 179°–80° C. (second recrystallization).

Example 9. N-Ethyl-2-(3,5-dibromo-2,6-dimethoxybenzamidomethyl) pyrrolidine hydrochloride Using the same method as for compound of Example 8 this compound is prepared from 20.4 g (0.06 mol) of 3,5-dibromo-2,6-dimethoxybenzoic acid, 50 ml of thionyl chloride and 7.7 g (0.06 mol) of 2-(aminomethyl)-1-ethylpyrrolidine. The obtained product is recrystallized from ethanol-ethyl ether. Yield: 20.2 g, m.p. 164°–65° C. The free base is precipitated from the water solution of the hydrochloric salt by the addition of sodium hydroxide, m.p. 133°–134° C.

Example 10. N-Ethyl-2-(3,5-dichloro-2,6-dimethoxybenzamidomethyl) pyrrolidine 20 ml of thionyl chloride is added to 11.9 g (0.047 mol) of 3,5-dichloro-2,6-dimethoxybenzoic acid. The mixture is heated on a steam bath for 30 minutes. To the solution is added 50 ml of toluene. The solvent and excess thionyl chloride is evaporated at reduced pressure. The residue is dissolved in 50 ml of dry ethyl ether. To the obtained solution is added dropwise while stirring 6.0 g (0.047 mol) of 2-(aminomethyl)-1-ethylpyrrolidine in 50 ml of ethyl ether. After 30 minutes at room temperature 300 ml of water is added while stirring. The water layer is separated and alkalized with sodium hydroxide solution which is added dropwise while stirring and cooling in ice. The precipitate is collected and washed with water. Yield: 9.0 g, m.p. 120°–21° C.

Example 11.
N-Ethyl-2-(3-bromo-5-chloro-2,6-dimethoxybenzamidomethyl) pyrrolidine.

20 ml of thionyl chloride is added to 11.82 g (0.04 mol) of 3-bromo-5-chloro-2,6-dimethoxybenzoic acid. The mixture is heated on a steam bath for 1 hour. To the solution is added 50 ml of toluene. The solvent and excess thionyl chloride is evaporated at reduced pressure. The residue is dissolved in 50 ml of dry methyl ethyl ketone. The solution is added dropwise while stirring to 5.13 g (0.04 mol) 2-(aminomethyl)-1-ethylpyrrolidine in 50 ml methyl ethyl ketone. After stirring for 30 minutes at room temperature 300 ml of ether is added. The obtained semisolid product is separated and dissolved in 300 ml of water. Sodium hydroxide solution is added while stirring and cooling in ice. The precipitate is collected and washed with water. Yield: 12.0 g, m.p. 124°–25° C.

Example 12.
N-Ethyl-2-(3,5-dibromo-2,6-dimethoxybenzamidomethyl) pyrrolidine 20 ml of thionyl chloride is added to 12.2 g (0.036 mol) of 3,5-dibromo-2,6-dimethoxybenzoic acid. The mixture is heated on a steam bath for 30 minutes. To the solution is added toluene and the solvent and excess thionyl chloride is evaporated at reduced pressure. To the residue is added dropwise while stirring a chloroform extract prepared as follows: 75 ml of 30% sodium hydroxide is added to 10.0 g (0.036 mol) of (+)-2-(aminomethyl)-1-ethyl-pyrrolidine d-tartrate. The mixture is extracted with 100 ml of chloroform and the extract is dried with magnesium sulphate.

After the addition of the chloroform extract the obtained solution is heated on a steam bath for 10 minutes. The solvent is evaporated and the residue is dissolved in 150 ml of water, acidified with hydrochloric acid, and extracted with ether. The water layer is alkalized with sodium hydroxide solution and the obtained precipitate is collected and washed with water. Yield: 7.0 g, m.p. 161°–62° C., $[\alpha]_D^{20°} = +53.4°$ (1% in acetone).

Example 13.
N-Ethyl-2-(3,5-dibromo-2,6-dimethoxybenzamidomethyl) pyrrolidine hydrochloride Using the same method as for compound in Example 12 this compound is prepared from 19.8 g (0.056 mol) of 3,5-dibromo-2,6-dimethoxybenzoic acid, 30 ml of thionyl chloride and 15.58 g (0.056 mol) of (−)-2-(aminomethyl)-1-ethylpyrrolidine l-tartrate. Yield: 14.3 g, m.p. 161°–62°, $[\alpha]_D^{20°} = -56.4°$ (0.4% in acetone). The free amine is converted to the hydrochloride by treating 13.0 g of the base in 50 ml of acetone with hydrogen chloride in ether. Yield: 13.5 g, m.p. 159°–60° C.

Example 14.
N-Ethyl-2-(3-bromo-2,6-dimethoxybenzamidomethyl) pyrrolidine hydrochloride 23.8 g (0.09 mol) of 3-bromo-2,6-dimethoxybenzoic acid is heated with 35 ml of thionyl chloride on a steam bath for 30 minutes. After the addition of toluene the excess thionyl chloride is evaporated at reduced pressure. To the residue is added dropwise while stirring a mixture of 12.6 g (0.09 mol) of triethylamine and a chloroform extract prepared as follows: 100 ml of 30% sodium hydroxide solution is added to 25.0 g (0.09 mol) of (−)-2-(aminomethyl)-1-ethylpyrrolidine l-tartrate. The mixture is extracted with 150 ml of chloroform and the extract is dried with magnesium sulphate. After the addition of the chloroform extract the obtained solution is heated on a steam bath for 10 minutes. The solvent is evaporated and the residue is dissolved in water, acidified with hydrochloric acid, and extracted with ether. The water layer is alkalized with sodium hydroxide and extracted with chloroform. The extract is dried with magnesium sulphate and the solvent is evaporated. The residual oil is dissolved in ether and acidified with hydrogen chloride. The obtained precipitate is collected by filtration. Yield: 20.3 g, m.p. 166°–68°, $[\alpha]_D^{20°} = -11.1°$ (0.5% in water).

Example 15.
N-Ethyl-2-(3-bromo-2,6-dimethoxybenzamidomethyl) pyrrolidine hydrochloride Using the same method as for compound in Example 14, except of the addition of triethylamine, this compound was prepared from 8.4 g (0.032 mol) of 3-bromo-2,6-dimethoxybenzoic acid, 20 ml of thionyl chloride and 9.0 g (0.032 mol) of (+)-2-(aminomethyl)-1-ethylpyrrolidine d-tartrate. Yield: 7.5 g, m.p. 166°–68° C., $[\alpha]_D^{20°} = 10.7°$ (0.5% in water).

In table 1 are summarized physical data for the compounds prepared according to the descriptions in Examples 6–15.

TABLE 1

N-Ethyl-2-(2,6-dialkoxybenzamidomethyl) pyrrolidines

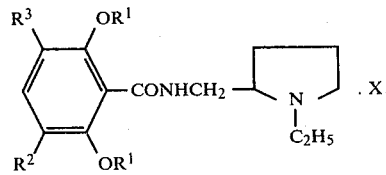

| Compound Prepared in Example | $R^1$ | $R^2$ | $R^3$ | X | M.p.°C. | C | H | N | O | Cl | Cl⁻ | Cl + Cl⁻ | Br |
|---|---|---|---|---|---|---|---|---|---|---|---|---|---|
| | | | | | | | | | | Calculated % Found | | | |
| 6 rac | CH₃ | H | H | HCl | 182–84 | 58.44 | 7.66 | 8.52 | | | 10.78 | | |

TABLE 1-continued
N-Ethyl-2-(2,6-dialkoxybenzamidomethyl) pyrrolidines

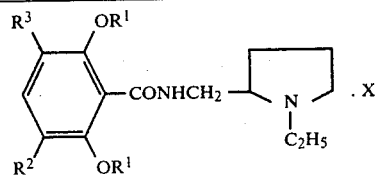

| Compound Prepared in Example | $R^1$ | $R^2$ | $R^3$ | X | M.p.°C. | C | H | N | O | Cl | $Cl^-$ | $Cl + Cl^-$ | Br |
|---|---|---|---|---|---|---|---|---|---|---|---|---|---|
| 7 rac | CH$_3$ | Br | H | HCl | 184–85 | 58.7<br>47.13<br>46.8 | 7.82<br>5.93<br>5.97 | 8.54<br>6.87<br>6.75 | 10.8 | 11.77<br>11.6 | | | |
| 8 rac | CH$_3$ | Cl | H | HCl | 179–80 | 52.90<br>52.9 | 6.66<br>6.9 | 7.71<br>7.64 | 13.21<br>13.2 | | 9.76<br>10.0 | 19.52<br>19.6 | |
| 9 rac | CH$_3$ | Br | Br | HCl | 164–65 | 39.49<br>39.5 | 4.76<br>4.73 | 5.76<br>5.47 | 9.86<br>9.88 | | 7.29<br>7.64 | | 32.84<br>32.7 |
| 10 rac | CH$_3$ | Cl | Cl | — | 120–21 | 53.19<br>53.4 | 6.14<br>6.29 | 7.76<br>7.55 | 13.29<br>13.1 | 19.63<br>19.6 | | | |
| 11 rac | CH$_3$ | Br | Cl | — | 124–25 | 47.36<br>47.3 | 5.47<br>5.69 | 6.91<br>6.79 | 11.83<br>11.6 | 8.74<br>8.52 | | | |
| 12 (+) | CH$_3$ | Br | Br | — | 161–62 | 42.69<br>42.7 | 4.93<br>4.83 | 6.22<br>6.06 | 10.66<br>10.8 | | | | 35.50<br>35.3 |
| 13 (−) | CH$_3$ | Br | Br | HCl | 159–60 | 39.49<br>39.39 | 4.76<br>4.73 | 5.76<br>5.88 | | | 7.29<br>7.15 | | |
| 14 (−) | CH$_3$ | Br | H | HCl | 166–68 | 47.13<br>47.07 | 5.93<br>5.91 | 6.87<br>6.87 | | | 8.70<br>8.85 | | |
| 15 (+) | CH$_3$ | Br | H | HCl | 166–68 | 47.13<br>47.0 | 5.93<br>6.00 | 6.87<br>6.71 | | | 8.70<br>8.77 | | |

The following examples illustrate how the compound of the present invention may be included in pharmaceutical preparations.

Example 16. Preparation of soft gelatin capsules 500 g of active substance were mixed with 500 g of corn oil, whereupon the mixture was filled in soft gelatin capsules, each capsule containing 100 mg of the mixture (i.e. 50 mg of active substance).

Example 17. Preparation of soft gelatin capsules 500 g of active substance were mixed with 750 g of pea nut oil, whereupon the mixture was filled in soft gelatin capsules, each capsule containing 125 mg of the mixture (i.e 50 mg of active substance.

Example 18. Preparation of tablets 50 kg of active substance were mixed with 20 kg of silicic acid of the trade mark Aerosil. 45 kg of potatoe starch and 50 kg of lactose were mixed therewith and the mixture was moistened with a starch paste prepared from 5 kg of potatoe starch and destilled water, whereupon the mixture was granulated through a sieve. The granulate was dried and sieved, whereupon 2 kg of magnesium stearate was mixed into it. Finally the mixture was pressed into tablets each weighing 172 mg.

Example 19. Preparation of effervescing tablets 100 g of active substance, 140 g of finely divided citric acid, 100 g of finely divided sodium hydrogen carbonate, 3.5 g of magnesium stearate and flavouring agents (q.s.) were mixed and the mixture was pressed into tablets each containing 100 mg of active substance.

Example 20. Preparation of a sustained release tablet 200 g of active substance were melted together with 50 g of stearic acid and 50 g of carnauba wax. The mixture thus obtained was cooled and ground to a particle size of at most 1 mm in diameter. The mixture thus obtained was mixed with 5 g of magnesium stearate and pressed into tablets each weighing 305 mg. Each tablet thus contains 200 mg of active substance.

PHARMACOLOGY

Introduction

An abundance of studies suggest that the antipsychotic action of neuroleptics is in some way related to the decrease in catecholamine transmission in the brain caused by these drugs and more specifically due to central dopamine (DA) receptor blockade as originally suggested by Carlsson (Acta Pharmacol. 20, 140–144, 1963; J. Neur. Transmission, 34, 125–132, 1973).

Most compounds with an antipsychotic action appear to affect several DA systems in the brain. It has been hypothesized that the antipsychotic action may be linked to blockade of DA receptors in the subcortical and cortical limbic structures (J. Pharm. Pharmacol. 25, 346, 1973; Lancet, nov. 6, 1027, 1976) or to blockade of DA receptors in the nigroneostriatal DA system (Intern. J. Neurol. 6, 27–45, 1967).

There are several techniques available to study DA receptor blockade in the brain. One method is based on the ability of anti-psychotics to block the behavioural effects induced by the DA agonist apomorphine. Apomorphine produces in rats and other species a characteristic syndrome consisting of repetitive movements (stereo-typies) and hyperactivity which appear to be due to activation of postsynaptic DA receptors in the brain (J. Pharm. Pharmacol. 19, 627, 1967; J. Neurol. Transm. 40, 97–113, 1977). The stereotypies (chewing, licking, biting) appear mainly to reflect action on DA receptors of the neostriatal system (J. Psychiat. Res., 11, 1, 1974) whereas the increased locomotion (hyperactivity) mainly appears to be due to activation of DA receptors in mesolimbic structures (nucleus olfactorium, nucleus accumbens), (J. Pharm. Pharmacol. 25, 1003, 1973).

A number of studies have demonstrated that neuroleptics block apomorphine stereotypies and that this blockade is well related to blockade of DA transmission measured by other techniques. Thus, the antiapomorphine effect coorelates with changes in DA turnover (Eur. J. Pharmacol., 11, 303, 1970), DA receptor binding studies (Life Science, 17, 993-1002, 1976) and most importantly with antipsychotic efficacy (Nature, 263, 388-341, 1976).

Methods

Male Sprague-Dawley rats weighing 225-275 g were used. The rats were observed in perspex cages (40 (L)×25 (w)×30 (h) cm) and the behaviour was scored 5, 20, 40, and 60 minutes after apomorphine. The compounds were injected 60 minutes prior to apomorphine hydrochloride (1 mg/kg) which was injected subcutaneously into the neck. This dose and form of administration was found to produce a very consistent response and very low variation in response strength. Furthermore, apomorphine given s.c. also produced a very consistent hyperactivity.

Directly after injection, the animals were placed in the cages, one in each cage. Scoring of the stereotypies were performed by two separate methods. The first scoring system was a modified version of the system introduced by Costall and Naylor (1973). The strength of the stereotypy was scored on a 0-3 scale as follows:

| Score | Description of stereotyped behaviour |
|---|---|
| 0 | No change in behaviour compared to saline controls or sedated. |
| 1 | Discontinous sniffing. |
| 2 | Continous sniffing. |
| 3 | Continous sniffing. Chewing, biting and licking. |

In the second system the number of animals displaying hyperactivity caused by apomorphine were scored. Each group consisted of 6-8 animals. Saline controls were always run simultaneously. $ED_{50}$'s are in the first scoring system (0-3 scale), the doses which reduce the strength of the stereotypies by 50% over the observation period of 60 minutes. $ED_{50}$'s of the second scoring system are the doses which reduce the number of animals showing hyperactivity by 50% over the observation period of 60 minutes. The $ED_{50}$'s were calculated from log dose-response curves by the method of least squares from 4-6 dose levels with 6-8 animals per dose level.

Results

The results are presented in Table 2. The compounds of the invention were compared with the antipsychotic sulpiride (Life Science, 17, 1551-1556, 1975). The tabulated results indicate that the compounds of the present invention are potent inhibitors of DA receptors in the brain. Due to their ability to antagonize both apomorphine stereotypies and hyperactivity they probably block DA receptors in both striatal and limbic areas (see Introduction). Furthermore they are considerably more active than the antipsychotic drug sulpiride. Since there is a highly significant correlation between the blockade of apomorphine and clinical antipsychotic efficacy (Nature, 263, 388-341, 1976), it is very likely that the compounds of the present invention will show a highly potent antipsychotic action in man.

TABLE 2

The ability to block apomorphine induced stereotypies and hyperactivity

| Compound according to Example No. | Stereotypies $ED_{50}$ μmol/kg i.p. | Hyperactivity $ED_{50}$ μmol/kg i.p. |
|---|---|---|
| 6 | 122 | 70 |
| 7 | 23 | 11 |
| 8 | 47 | 30 |
| 9 | 5.3 | 1.8 |
| 10 | 5.8 | 3.0 |
| 11 | 6.2 | 3.9 |
| 12 | >178 | ~11 |
| 13 | 3.3 | 0.33 |
| 14 | 5.6 | 0.83 |
| 15 | >196 | ~123 |
| Sulpiride | 293 | 50 |

The compounds of the invention were also compared to sulpiride in the same test system after oral administration. The results are tabulated below.

TABLE 3

| Compound acc. to Example No. | Stereotypies $ED_{50}$ μmol/kg p.o. | Hypractivity $ED_{50}$ μmol/kg. p.o. |
|---|---|---|
| 7 | 47 (19 mg/kg) | 17 (7 mg/kg) |
| 9 | 8.2 (4.0 mg/kg) | 5.5 (2.7 mg/kg) |
| Sulpiride | >586 (>200 mg/kg) | >586 (>200 mg/kg) |

As can be seen sulpiride has lost all activity. This is in contrast to the tested compounds of the invention, which are still effective after oral administration.

I claim:

1. A compound of the formula

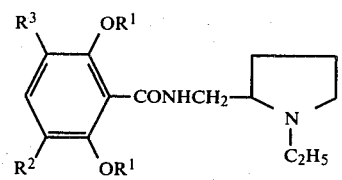

or a pharmaceutically acceptable salt thereof, in which formula $R^1$ represents an alkyl group with 1-3 carbon atoms, $R^2$ and $R^3$ are the same or different and each represents a hydrogen, chlorine or bromine atom.

2. A compound according to claim 1 with the formula I wherein $R^1$ is an alkyl group with 1-3 carbon atoms and $R^2$ and $R^3$ are the same or different and each represents a hydrogen, chlorine or bromine atom, provided that $R^2$ is chlorine or bromine when $R^3$ is hydrogen.

3. A compound according to claim 1 with the formula I wherein $R^1$ is a methyl group and $R^2$ and $R^3$ are the same or different and each represents a chlorine or a bromine atom.

4. A compound according to any of claims 1, 2 or 3 in the form of a substantially pure stereoisomer.

5. A pharmaceutical preparation which comprises as active ingredient at least one compound of the formula

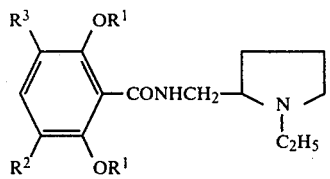

or a pharmaceutically acceptable salt thereof, in an amount effective to block the central dopamine receptors of the brain in which formula $R^1$ represents an alkyl group with 1–3 carbon atoms, $R^2$ and $R^3$ are the same or different and each represents a hydrogen, chlorine or bromine atom, in association with a pharmaceutically acceptable carrier.

6. A pharmaceutical preparation comprising as active ingredient an amount effective to block the dopamine receptors of the brain of a compound according to claims 2 or 3 in association with a pharmaceutically acceptable carrier.

7. A pharmaceutical preparation which comprises as an active ingredient an amount effective to block the dopamine receptors of the brain of a compound according to claims 2 or 3 in the form of a substantially pure stereoisomer in association with a pharmaceutically acceptable carrier.

8. A pharmaceutical preparation according to claim 5 in dosage unit form.

9. A pharmaceutical preparation which comprises as an active ingredient an amount effective to block the dopamine receptors of the brain of a compound according to claims 2 or 3 in association with a pharmaceutically acceptable carrier in dosage unit form.

10. A pharmaceutical preparation which comprises as an active ingredient an amount effective to block the dopamine receptors of the brain of a compound according to claims 2 or 3 in the form of a substantially pure stereoisomer in association with a pharmaceutically acceptable carrier in dosage unit form.

11. A method for the treatment of psychoses in man, characterized by the administration to a host in need of such treatment of an effective amount of a compound of the formula

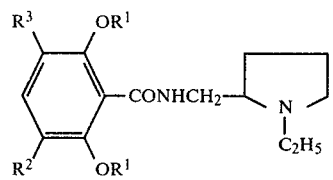

or a pharmaceutically acceptable salt thereof, in which formula $R^1$ represents an alkyl group with 1–3 carbon atoms, $R^2$ and $R^3$ are the same or different and each represents a hydrogen, chlorine or bromine atom.

12. A method for the treatment of psychoses according to claim 11, characterized by the administration to a host in need of such treatment of an effective amount of a compound according to any of claims 2 or 3.

13. A method for the treatment of psychoses in man characterized by the administration to a host in need of such treatment of an amount effective to block the dopamine receptors of the brain of a compound according to claims 1, 2 or 3 in the form of a substantially pure stereoisomer.

* * * * *